US010124085B2

(12) United States Patent
Sahin et al.

(10) Patent No.: US 10,124,085 B2
(45) Date of Patent: Nov. 13, 2018

(54) ANTIMICROBIAL AND ANTIVIRAL HYGIENIC PRODUCTS

(71) Applicant: YEDITEPE UNIVERSITESI, Istanbul (TR)

(72) Inventors: Fikrettin Sahin, Istanbul (TR); Zeynep Ustaoglu, Istanbul (TR); Selami Demirci, Istanbul (TR); Okan Demir, Istanbul (TR); Ayla Burcin Asutay, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 0 days.

(21) Appl. No.: 15/531,465

(22) PCT Filed: Nov. 23, 2015

(86) PCT No.: PCT/TR2015/050191
§ 371 (c)(1),
(2) Date: May 29, 2017

(87) PCT Pub. No.: WO2016/085434
PCT Pub. Date: Jun. 2, 2016

(65) Prior Publication Data
US 2017/0319737 A1   Nov. 9, 2017

(30) Foreign Application Priority Data

Nov. 27, 2014 (TR) .................................. 2014/14155

(51) Int. Cl.
| | | |
|---|---|---|
| A61F 13/20 | (2006.01) | |
| A61F 13/51 | (2006.01) | |
| A61F 13/84 | (2006.01) | |
| A61L 15/18 | (2006.01) | |
| A61L 15/20 | (2006.01) | |
| A61L 15/44 | (2006.01) | |
| A61L 15/46 | (2006.01) | |
| A61L 15/60 | (2006.01) | |
| A61F 13/511 | (2006.01) | |

(52) U.S. Cl.
CPC .......... *A61L 15/44* (2013.01); *A61F 13/2074* (2013.01); *A61F 13/51113* (2013.01); *A61F 13/8405* (2013.01); *A61L 15/18* (2013.01); *A61L 15/20* (2013.01); *A61L 15/46* (2013.01); *A61L 15/60* (2013.01); *A61F 2013/51059* (2013.01); *A61F 2013/8414* (2013.01); *A61L 2300/10* (2013.01); *A61L 2300/202* (2013.01); *A61L 2300/206* (2013.01); *A61L 2300/216* (2013.01); *A61L 2300/232* (2013.01); *A61L 2300/406* (2013.01); *A61L 2300/408* (2013.01)

(58) Field of Classification Search
None
See application file for complete search history.

(56) References Cited

U.S. PATENT DOCUMENTS

| | | | |
|---|---|---|---|
| 4,405,323 A | 9/1983 | Auerbach | |
| 4,896,768 A | 1/1990 | Anderson | |
| 5,885,263 A | 3/1999 | Gancet et al. | |
| 6,248,733 B1 * | 6/2001 | Landgrebe | A01N 55/02 514/184 |
| 6,488,948 B1 | 12/2002 | Danieli | |
| 2003/0157149 A1 | 8/2003 | Syverson et al. | |
| 2005/0250404 A1 * | 11/2005 | Clarke | A47L 13/20 442/340 |
| 2007/0044801 A1 * | 3/2007 | Mathis | A41D 13/11 128/206.19 |
| 2007/0167543 A1 * | 7/2007 | Schwesig | A01N 59/14 524/100 |
| 2008/0057134 A1 * | 3/2008 | Crudden | A61K 33/36 424/617 |
| 2008/0132632 A1 * | 6/2008 | Schiraldi | C08K 9/08 524/445 |
| 2010/0069861 A1 | 3/2010 | Yao et al. | |

FOREIGN PATENT DOCUMENTS

| | | |
|---|---|---|
| WO | WO2008062291 A2 | 5/2008 |
| WO | WO2013072883 A1 | 5/2013 |

OTHER PUBLICATIONS

Kaduk J. A., Fab E.J., "Crystal structure of zeolite Y as a function of ion exchange" The Rigaku Journal, 12:14-34, 1995.
Hanke W., and K. Moeller, "Near-infrared study of the dealumination and water desorption from zeolites", Zeolites, 4:244-250, 1984.
Kawahara, K., K. Tsuruda, M. Morishita, and M. Uchida, "Antibacterial effect of silver-zeolite on oral bacteria under anaerobic conditions", Dental Materials, 16:452-455, 2000.
Galeano, B., E. Koff, and W. L. Nicholson, "Inactivation of vegetative cells, but not spores, of *Bacillus anthracia, B. cereus*, and *B. subtilis* on stainless steel surfacescoated with an antimicrobial silver-and zinc-containing zeolite formulation", Applied and Environmental Microbiology, 69:4329, 2003.
Yamaguchie. E., F. Valena, S. M. Smith, A. Simmons, and R. H. Eng, "Colonization pattern of vancomycin-resistant Enterococcus faecium", American Journal of Infection Control, 22:202-206, 1994.
Yoshikawa, T., M. Ihira, S. Suzuki. S. Suga, A. Tomitaka, H. Ueda, and Y. Asano, "Rapid contamination of the environments with varicella-zoster virus DNA from a patient with herpes zoster", Journal of Medical Virology, 63:64-66, 2001.

(Continued)

*Primary Examiner* — Robert A Wax
*Assistant Examiner* — Randeep Singh
(74) *Attorney, Agent, or Firm* — Gokalp Bayramoglu

(57) ABSTRACT

The present invention relates to hygienic products such as sanitary pads and tampons, patient/adult diapers and baby diapers which are made antimicrobial. In the present invention, a mixture of glucopon, chlorhexidine gluconate and triclosan is obtained from the boron compounds called sodium borate, zinc borate, sodium perborate tetrahydrate, borax pentahydrate and disodium octaborate tetrahydrate; and this mixture provides antifungal, anticandidal, antibacterial and antiviral properties to the woven or non-woven textile products and hygienic products. Additionally, the said hygienic products are made hydrophilic by means of the invention.

12 Claims, 3 Drawing Sheets

(56) References Cited

OTHER PUBLICATIONS

Bailey P. J., G. Cousins, G. A. Snow, and A.J. White, "1. Boron-Containing Antibacterial Agents: Effects on Growth and Morphology of Bacteria Under Various Culture Conditions" Antimicrobial Agents and Chemotherapy, 17:549, 1980.

Benkovic S.J., S.J. Baker, and Alley M.R., "Identification of borinic esters as inhibitors of bacterial cell growth and bacterial methyltransferases, CcrM and MenH". Journal of Medicinal Chemistry. 48:7468-7476, 2005.

Reynolds, R.C., Campbell S.R., Fairchild R.G., Kisliuk R.L., Micca P.L., Queener S.F., Riordan J.M., SedwickW.D., Waud W.R., Leung A.K.W., Dixon R.W., Suling W.J., and BorhaniD.W., Novel boron-containing, nonclassical antifolates: Synthesis and preliminary biological and structural evaluation.Jaurnal of Medicinal Chemistry,50:3283-3289,2007.

Qin G., S. Tian, Z. Chan, and B. Li, "Crucial role of antioxidant proteins and hydrolytic enzymes in pathogenicity of Penicillium expansum", Molecular & Cellular Proteomics, 6:425-438, 2007.

Qin G.,Y. Zong, Q. Chen, D. Hua, and S. Tian, "Inhibitory effect of boron against Botrytis cinerea on table grapes and its possible mechanisms of action", International Journal of Food Microbiology 138:145-150, 2010.

Hennessey, T. D., "Some antibacterial properties of chlorhexidine", Journal of Periodontal Research, 8: 61-67, 1973.

Regos, J., O. Zak, R. Soli, WA. Visher and EG. Wench, "Antimicrobial spectrum of triclosan a broad spectrum antimicrobial agent for topical application, II: comparison with other antimicrobial agents." Dermotologicia, 158:72-9, 1979.

Bernstein, D., G. Schiff, G. Echier, , A. Prince, M. Feller and W. Briner, "In vitro virucidal effectiveness of a 0.12%-chlorhexidine gluconate mouthtinse", J Dent Res., 69(3):874-6, 1990.

Bailey, A., and M., Longson, "Virucidal Activity of Chiorhexidine on Strains of Herpesvirus hominis, Poliovirus, and Adenovirus", J Clin Pathol., 25:76-78, 1972.

Lalitha, M. K. and T. N. Vellore, "Manual on antimicrobial susceptibility tenting", URL: http://www.ijmm.org/documents/Antimicrobial. doc, 2005.

* cited by examiner

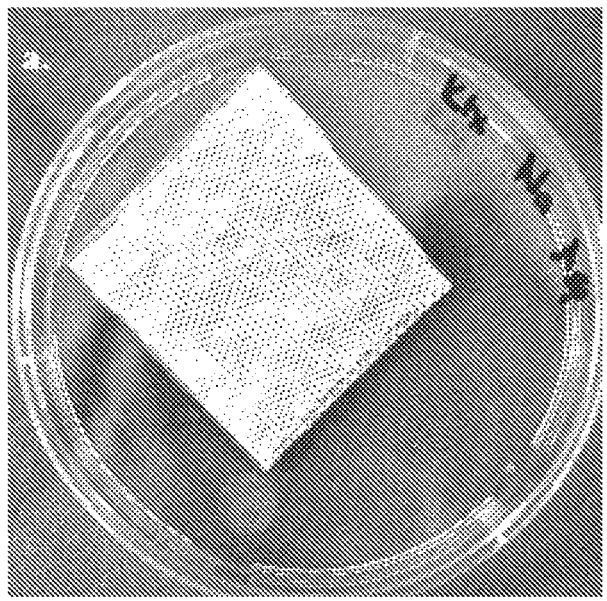
Figure 1-a
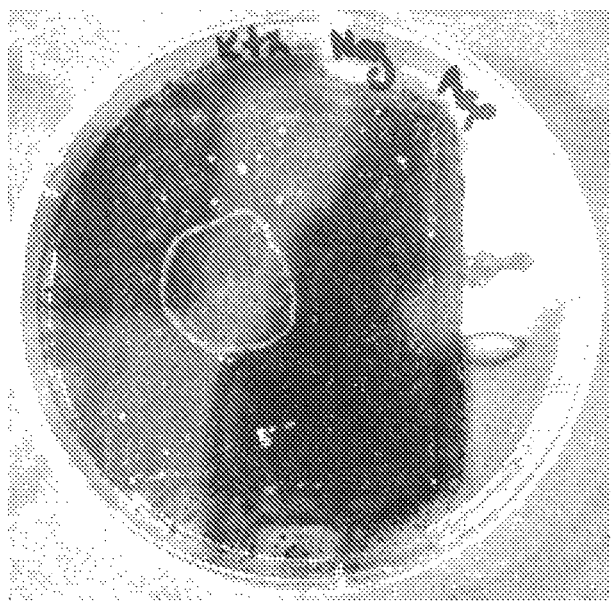
Figure 1-b

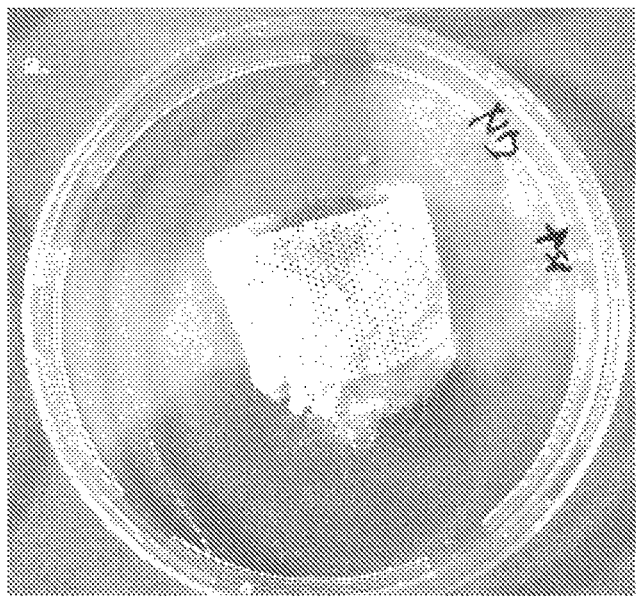
Figure 2-a
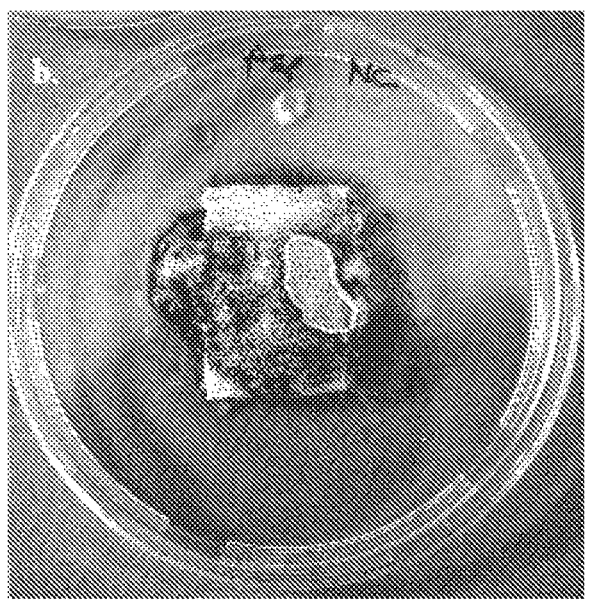
Figure 2-b

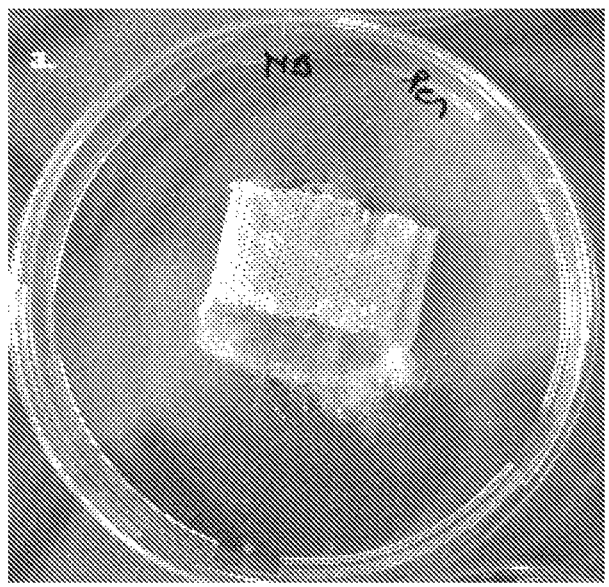
Figure 3-a
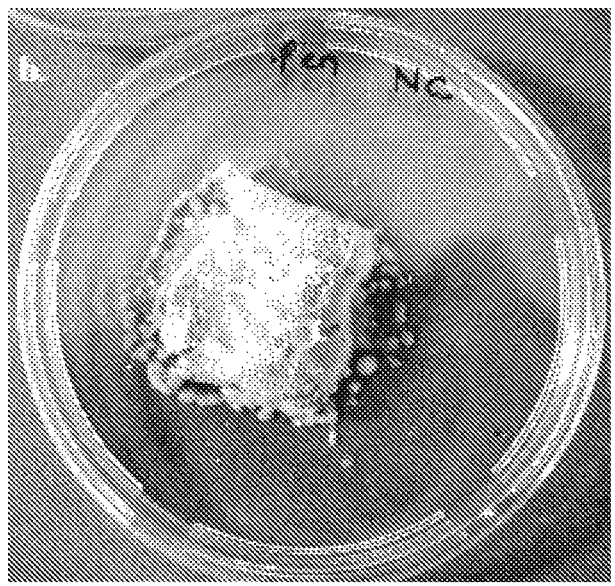
Figure 3-b

ANTIMICROBIAL AND ANTIVIRAL HYGIENIC PRODUCTS

CROSS REFERENCE TO RELATED APPLICATIONS

This application is the national phase entry of International Application No. PCT/TR2015/050191, filed on Nov. 23, 2015, which is based upon and claims priority to Turkish Patent Application No. TR2014/14155, filed on Nov. 27, 2014, the entire contents of which are incorporated herein by reference.

TECHNICAL FIELD OF THE INVENTION

The present invention relates to hygienic products such as sanitary pads, bladder pads, tampons, patient and baby diapers which are made antimicrobial and antiviral.

BACKGROUND OF THE INVENTION

Use of hygienic products for children, patients and women in the world has been observed to increase as the social life has developed and conventional methods have been abandoned. Since these products are not sterile and antimicrobial, microorganisms can easily proliferate in these media which are damp and include nutrition, and thus may cause important diseases in people. The content of the blood discharged from the bodies of women during menstruation provides a suitable medium for reproduction of microorganisms. These microorganisms reproduce on the hygienic pads or tampons used by women during menstruation period and cause serious diseases that threaten health. In addition, diapers fastened to the babies who cannot control their bladders and bowel movements or patient/aged diapers used by patients who are in need of care are also suitable reproduction media for opportunistic pathogens.

Especially in women using sanitary pads, infections that may occur due to closeness of the reproductive organs to the bowels and urinary tract anatomically cause a threat to the reproductive organs. While the fact that the vagina has low pH during normal times and that there is a form obstructing passage from the urethra to the bladder minimizes vaginal infection risk, a suitable medium is formed for reproduction of microorganisms because the menstruation blood is rich in nutrients during menstruation period and normalizes pH level of the vagina. Formation of a suitable medium for reproduction of microorganisms, rich nutrients in the blood and the dampness on the pad that is used increase infection risk. If the pads that are used are not frequently replaced, infections of reproduction system and urinary tract are encountered. In order to prevent infections and the odor occurring in long term use of pads, pads should be preventing microbial growth.

Tampons, which are another product used by women during menstruation period, retain the blood discharged from the body through vagina during menstruation period just like hygienic pads. Vaginal tampons, differing from the sanitary pads, enable absorbance of the blood before the blood is discharged out of the vagina. Factors that make social life of women difficult as a result of use of pads can be eliminated by use of tampons. Menstruation blood produces a special odor when it contacts with air. In tampons however the odor is eliminated since the blood does not contact with air. Although vaginal tampons make life easier in menstruation periods and do not pose risks when used appropriately, they may cause life threating situations when used incorrectly. For example, life threatening diseases such as septic shock caused by the bacterium *Staphylococcus aureus* may occur due to the blood waiting too long in the vagina. The bacteria at the genital region rapidly proliferate in septic shock and the toxins they produce pass to the blood of the user. Tampons should be frequently changed in order to prevent this situation. However, the best precaution that can be taken is to have the tampons possess microbial growth preventing properties.

Since babies cannot control their bladders and bowel movements, they urinate and defecate uncontrollably. To this end, nowadays paper based disposable baby diapers are used. Feces of babies have an irritating effect on the sensitive skins of babies. The thin fat layer on the surface of the skin irritates the skin as it passes moisture and feces. Occasionally irritations called diaper rashes, which appear bright red, occur on the babies' bottoms. Increase of heat and moisture on the irritated skin create a suitable medium for reproduction of some microorganisms and thus the rash gets "infected". The factor which is accepted as the reason for development of rash on the skin is the ammonia released under the effect of the bacterium *Bacillus ammoniagenes* which breaks down urea. In the studies that were conducted, *Staphylococcus aureus* were found on the skin area where rash is observed; however, whether this bacterium is the primary reason or a secondary reason of the rash has not yet been clarified. In 85% of the findings which is a substantial amount, the species *Candida albicans* was detected at the rash area. Similar to the bacterial case, it has not yet been clarified whether *Candida albicans* infection is the primary or secondary cause of the rash formation. However, it has been identified that either of these microorganisms causes the infected rash. Problems encountered in baby diapers can also occur in patient diapers.

There are studies in the state of the art on the antimicrobial properties of some boron compounds. Bailey et al. (1980) found, with the experiments they conducted, that boric acid has antibacterial activity on enteric bacteria. Antimicrobial agents containing boron were tried on gram negative bacteria (*Escherichia coli* and *Proteus mirabilis*) and were observed to be effective.

Additionally, in a study by Benkovic et al (2005), it was observed that boric esters have a broad spectrum antibacterial activity. Results of their study reveal that boric esters inhibit DNA methyl transferase in gram negative and positive bacteria.

Reynold et al. (2007) indicated that lipophilic 2,4-diamino-6-methylpyrimidine antifolate compound, which comprises two different borons, has a moderate level antibacterial activity against the bacteria *Mycobacterium avium* and *Lactobacillus casei*. In addition, it is shown that some boron derivatives have antifungal activities.

A study by Qin et al. (2007) showed that potassium tetraborate has an inhibitory effect on micelle growth of *Penicillium expansium*. It was determined that 0.1% concentration of potassium tetraborate is the minimum concentration preventing micelle growth. Qin et al. (2010) also searched for the effects of potassium tetraborate on *Botrytis cinerea* which is the pathogen leading to gray mold disease. They showed that they could control this mold causing disease on the grapes by using potassium tetra borate with 1% concentration. However, in none of the said studies were developed boron added antimicrobial sanitary pads, tampons, baby diapers and patient diapers.

A study by Hennessey (2006) showed that a 10-minute exposure of various bacterial strains to 0.02% chlorhexidine solution lead to 99.99% inhibition of these microorganisms.

A study by Regos et al. indicates that triclosan is 10 to 100 times more effective than hexachlorophene on *Escherichia coli, Klebsiella edwardsii* and *Salmonella* spp. but is less effective on streptococci, micrococci, and *Propionibacterium acnes*. The study also revealed that even the low-concentration of triclosan had a broad spectrum effect on both gram negative and gram positive bacteria, especially on *Proteus vulgaris, Salmonella* spp., mycobacteria and anaerobic bacteria.

In a study by Bernstein et al (1990), activities of 0.12% chlorhexidine gluconate containing mouthrinse (Peridex) against herpes simplex virus (HSV) related with tooth decay, cytomegalovirus (CMV), influenza A, parainfluenza, polio, and hepatitis B (HBV) virus were researched and the results indicated that it was effective against all the viruses, except polio virus, within 30 seconds.

A study by Bailey and Longson (1972) indicates that while 0.02% chlorhexidine gluconate reduced the virus titration of Herpesvirus hominis by more than 99% at the end of a 90-minute exposure at room temperature, it remained ineffective against poliovirus and adenovirus.

In the US patent documents numbered U.S. Pat. No. 4,896,768 and U.S. Pat. No. 6,488,948, in the state of the art, antibacterial sanitary pads were developed. Additionally the US patent document numbered U.S. Pat. No. 4,405,323 discloses about development of an antibacterial tampon to prevent septic shock. However, it was not indicated whether the said products have any effect on fungi, yeasts and viruses.

The above-mentioned inventions do not disclose antifungal, anticandidal and antiviral activities; the said applications are intended only against bacteria.

SUMMARY OF THE INVENTION

An objective of the present invention is to provide antifungal hygienic products.

Another objective of the present invention is to provide anticandidal hygienic products.

A further objective of the present invention is to provide antibacterial hygienic products.

Another objective of the present invention is to provide antiviral hygienic products.

Another objective of the present invention is to provide antimicrobial (antifungal, anticandidal, antibacterial, antiviral) property to sanitary pads, tampons, baby diapers, patient/adult diapers.

A further objective of the present invention is to provide hygienic products which prevent fermentation odors by preventing microorganism growth.

Another objective of the present invention is to provide hygienic products which prevent formation of allergies, rashes and open sores caused by frequently encountered infections in women, children and elderly/patients at the areas where the hygienic products are used.

A further objective of the present invention is to enable to develop a hydrophilic textile material (woven and nonwoven fabrics).

BRIEF DESCRIPTION OF THE DRAWINGS

Antimicrobial and antiviral hygienic products developed to fulfill the objectives of the present invention are illustrated in the accompanying figures, in which:

FIG. 1-*a* is a view of antifungal effect of a sanitary pad containing sodium borate $((Na_2O)(B_2O_3).10H_2O)$ against *Aspergillus niger*.

FIG. 1-*b* is a view of *Aspergillus niger* growth on a sanitary pad not containing sodium borate $((Na_2)(B_2O_3)_5.10H_2O)$.

FIG. 2-*a* is a view of antifungal effect of a tampon containing sodium borate $((Na_2O)(B_2O_3)_5.10H_2O)$ against *Aspergillus niger*.

FIG. 2-*b* is a view of *Aspergillus niger* growth on a tampon not containing sodium borate $((Na_2)(B_2O_3)_5.10H_2O)$.

FIG. 3-*a* is a view of antifungal effect of a tampon containing zinc borate $(2ZnO.3B_2O_3.3.5H_2O)$ against *Penicillium* spp.

FIG. 3-*b* is a view of *Penicillium* spp. growth on a tampon not containing zinc borate $(2ZnO.3B_2O_3.3.5H_2O)$.

DETAILED DESCRIPTION OF THE INVENTION

In all of the tests standard hygienic products not containing boron compounds are used as the negative control.

Within the scope of the invention; applications were made on hygienic sanitary pads, tampons, baby diapers, patient diapers by using sodium borate $((Na_2O)(B_2O_3)_5.10H_2O)$, zinc borate $(2ZnO.3B_2O_3.3.5H_2O)$, sodium perborate tetrahydrate $(NaBO_3.4H_2O)$, borax pentahydrate $(Na_2B_4O_7.5H_2O)$ and disodium octaborate tetrahydrate $(Na_2B_8O_{13}.4H_2O)$ boron compounds and glucopon, chlorhexidine gluconate, triclosan; and thus hygienic products with new properties are obtained.

Experimental Studies
Antimicrobial Tests
Modified Disc Diffusion Method

Standard NCCLS disc diffusion method [21] was used by being modified in order to determine the antimicrobial activity of boron compounds on each microorganism that is being tested. The 100 id solution containing $10^8$ cfu/ml of bacteria, $10^6$ cfu/ml of yeast and $10^4$ spore/ml of fungi was prepared with new cultures and was inoculated with spreading method on Nutrient Agar (NA), Sabouraud Dextrose Agar (SDA) and Potato Dextrose Agar (PDA), respectively. 20 µl of sterile water was dropped on the empty discs and it was separately immersed into pulverized zinc borate, sodium borate, sodium perborate tetrahydrate, borax pentahydrate, disodium octaborate tetrahydrate. The discs coded with zinc borate, sodium borate, sodium perborate tetrahydrate, borax pentahydrate, disodium octaborate tetrahydrate were placed in inoculated petri dishes. 20 µl sterile water dropped empty discs were used as negative control. As for positive control, Ofloxacin (10 µg/disc) and nystatin (30 µg/disc) were used for bacteria and fungi, respectively. The petri dishes, which were inoculated and on which modified disc diffusion method was applied, were kept at 36±1° C. for bacteria for 24 hours and for yeasts for 48 hours and at 25±1° C. for fungi for 72 hours. Antimicrobial activity against microorganisms tested with modified disc diffusion method was assessed by observing the inhibition zone (zone where microorganisms do not grow). Antimicrobial activity test results of the tested boron compounds are summarized in Table 1. All tests were repeated at least twice.

Method of Obtaining Hygienic Products Containing Boron Compounds, Chlorhexidine Gluconate, Triclosan Zinc borate, sodium borate, sodium perborate tetrahydrate, borax pentahydrate and disodium octaborate tetrahydrate of different concentrations (0.05-50 mg/cm$^2$) are mixed with SAP (superabsorbent) material. Then, they are dispersed to the layer of the baby diapers and pads between the water absorbent inner surface and impermeable outer surface. The said mixture is dispersed homogeneously to the absorbent inner layer of the tampon.

In order to increase absorbance of the surface contacting the skin and to provide antimicrobial property;

for 1000 g solution, 0.3 g triclosan is mixed in 70 g Glucopon 215 CS UP©, until it becomes homogenous, 75 g 20% chlorhexidine gluconate is added to the mixture and the solution is homogenized by the help of a homogenizer, 854.7 g distilled water is added to the obtained solution and mixed for 1-1.5 hours, pH value of the solution is brought to 5-7 by the help of citric acid or acetic acid.

The prepared solution is transferred to a holding tank, and the textile material, on which it will be applied, is immersed therein so as to completely cover the surface; it is kept therein for 5-10 minutes and then is completely dried at 25-90° C.

Antimicrobial activity tests of sections of the developed baby diapers, tampons, sanitary pads and patient/adult diapers prepared at sizes of 4×4 cm and 1×1 cm were performed via the below mentioned methods.

Antimicroblal Tests

Antimicrobial activity tests of sanitary pads, tampons, baby diapers, and patient/adult diapers prepared as described above with zinc borate, sodium borate, sodium perborate tetrahydrate, borax pentahydrate and disodium octaborate tetrahydrate were performed simultaneously by two different methods.

In the first test method; isolates from the bacteria *Escherichia coli, Staphylococcus aureus, Pseudomonas aeruginosa*; the yeasts *Candida albicans* and *Candida glabrara* and the fungi *Aspergillus niger, Botrytis cinerea, Fusarium oxysporum, Penicilliun vinaceum, Penicilliurn expansum* were inoculated on petri dishes containing suitable media (NA, SDA and PDA respectively). Absorbent parts of the boron added hygienic products with hydrophilic surfaces containing chlorhexidine and triclosan and prepared in a size of 1×1 cm were placed on the inoculated petri dishes such that they touch the medium surface. The inoculated petri dishes were incubated for 24 hours for bacteria and 48 hours for yeasts at 36±1° C. and 72 hours for fungi at 25±1° C. Antimicrobial activities of hygienic products were assessed by observing the inhibition zone (zone where microorganisms do not grow) formed around the samples on which application is made.

In the second method, the boron-containing or not-containing pad, tampon and baby diaper surfaces having a size of 4×4 cm placed in empty petri dishes are contaminated by 100 µl of the solutions (containing $10^8$ cfu/ml bacteria, $10^6$ cfu/ml yeast and $10^4$ spore/ml fungi) prepared from the fresh media prepared within the buffer solution. The contaminated hygienic products were incubated at 36±1° C. for bacteria and yeasts, and at 25±1° C. for fungi. It was determined whether there was microbial growth on the surfaces of the tested hygienic product surfaces by performing regressive isolation in intervals of 1, 3 and 6 hours.

According to the pretesting results, it was determined that among the concentrations that were used, 4 mg/cm² zinc borate, 4 mg/cm² sodlam borate, 5.5 mg/cm² sodium perborate tetrahydrate, 5.5 mg/cm² borax pentahydrate and 5.5 mg/cm² disodium octaborate tetrahydrate gave the most effective antimicrobial (antifungal, anticandidal and antibacterial) results. Then the above summarized experiments were continued for only the most effective concentrations of boron compounds with 3 repetitions. The results are summarized in Table 2.

Experimental studies were carried out with certain fungi, yeast and bacteria species.

Among these microorganisms, the bacteria were *Escherichia coli, Staphylococcus aureus,* and *Pseudomonas aeruginosa*.

The yeasts used in the experimental studies were *Candida albicans* and *Candida glabrata* and the fungi used in the same were *Fusarium oxysporum, Botrytis cinerea, Aspergillus niger, Penicillirm vinaceum* and *Penicillium expansum*.

Antiviral Tests

Antiviral Activity Tests of Chlorhexidine Gluconate;

In order to produce Human adenovirus type 5 Adenoid 75 strain and Poliovirus type 1 Chat strain virus and to carry out the experiment, a complete layer of HEp-2 cells (ATCC CCL-23), which are human monolayer tumor cells, were used. For determining virus titration, reference Human adenovirus type 5 Adenoid 75 strain and Poliovirus type 1 Chat strain were inoculated by making serial dilutions to HEp-2 cells, and by taking as basis the virus dilution that produces a cytopathic effect visible in invert microscope, virus titration was computed by using Spearman-Karber method. In order to determine Sub-Cytotoxic concentration of Chlorhexidine gluconate, Chlorhexidine gluconate was 10-fold serially diluted with Eagle's minimum essential medium (MEM) and non-toxic concentration was detected in the cell culture and non-toxic concentration was used in the antiviral tests. For the controls, MEM inoculated HEp-2 cells, full layer HEp-2 cells wherein Chlorhexidine gluconate could not be added, 10-fold diluted reference virus titration control, formaldehyde control and controls containing toxic concentrations of Chlorhexidine gluconate were used as negative control instead of the virus.

Preparation of Cell Culture Medium and the Chemicals

Mem Medium:

10% serum (FBS) containing enzymes, hormones and growth factors for the cells to adsorb to the surfaces and proliferate; and 40 IU/ml penicillin, 0.04 mg/ml streptomycin, 0.5 mg/ml glutamine to prevent fungi and bacteria contamination; and 1% sodium bicarbonate as a buffer solution were added therein. (FBS: Inactivated and without mycoplasma), (Sodium bicarbonate: Sterile 7.5% solution)

Medium Used in Virus Inoculation:

The medium included 1% antibiotic (Penicillin, Streptomycine, Amphotericin B) in order to prevent fungi and bacteria contamination, and 1% sodium bicarbonate as a buffer solution. FBS serum was not added to this medium.

Hard Water Preparation:

Solution A: 19.84 g nonaqueous magnesium chloride (MgCl2) or hydrated magnesium chloride and 46.24 g nonaqueous calcium chloride ($CaCl_2$) or hydrated calcium chloride in water are dissolved in water of the same equal amount. It is diluted to 1000 ml and autoclaved.

Solution B: 35.2 g sodium bicarbonate ($NaHCO_3$) is dissolved in water and diluted to 1000 ml. It is filtered (mesh size should be 0.22 µM).

Hard Water:

6.0 ml Solution A and 8.0 ml solution B are added to 600 ml water.

It is stirred and diluted to 1000 ml.

pH value of the hard water should be 7.0±0.2.

40 g/l sodium hydroxide (NaOH) (1 mol/l) or hydrochloric acid (HCl) (1 mol/l) is used to adjust pH value.

It should be prepared in sterile conditions and used within 12 hours.

Preparation of Clean and Polluted Media

Clean medium; 0.3 gr Bovine Serum Albumin Fraction V is dissolved in 100 ml sterile water. The solution that is obtained is sterilized by being passed through a filter with mesh size 0.22 µM.

Polluted medium: sheep erythrocyte and BSA are used for the polluted medium. 3 g BSA is dissolved in 100 ml sterile water and filtered. 3 ml sheep erythrocyte was completed to 97 ml BSA.

Erythrocyte; 8 ml fresh sheep blood was rotated at 800 G for 10 minutes and then its supernatant was removed; upon adding 8 ml phosphate buffer salt (PBS), pipetting was performed and it was again rotated at 800 G for 10 minutes. This procedure was repeated three times.

Analysis

Firstly, liquid chlorhexidine gluconate was solid serially diluted with the cell culture medium (MEM) and its non-toxic concentration in cell culture was calculated. 8 ml of the chlorhexidine gluconate that will be tested was mixed with 2 ml hard water. The obtained solution was serially diluted (dilution step 1:10) with MEM and incubated in 96-well monolayered cells. The microscopic changes that occurred were recorded. Concentrations that showed cytopathic effect (CPE) were determined. Chlorhexidine gluconate and formaldehyde CPE values were compared. After determining non-toxic concentration of chlorhexidine gluconate on the cells, the effect of chlorhexidine gluconate on virus titration as a result of 1-60 minutes application periods in clean and polluted media was studied. For the controls, MEM inoculated HEp-2 cells, fill layer HEp-2 cells wherein Chlorhexidine gluconate could not be added, 10-fold diluted reference virus titration control, formaldehyde control and controls containing toxic concentrations of Chlorhexidine gluconate were used as negative control instead of the virus.

Taking as basis the virus dilutions wherein cytopathic effect that is visible in invert microscope is formed, virus titration was calculated as $TCID_{50}$ value by using Spearman-Karber method.

According to TS EN 14476 (MARCH 2007) standard, disinfectants should reduce virus titration by 4 or more logs for their antiviral activities.

Antiviral Activity Tests of Glucopou Solution:

8% Glucopon which was used for making the surfaces hydrophilic was tested on Human Herpes simplex virus type 1 (HSV-1) MachIntyre strain as described above. Taking as basis the virus dilutions which are seeded by performing serial dilutions to Vero (ATCC CCL-81) cells and wherein cytopathic effect that is visible in invert microscope is formed, virus titration was calculated as $TCID_{50}$ value by using Spearman-Karber method.

Antiviral Activity Tests of Mixture of Chlorhexidine Gluconate, Glucopon and Triclosan:

As mentioned before, a solution containing Chlorhexidine gluconate, Glucopon and Triclosan which will be applied to a surface was prepared as follows: for 1000 g solution, 0.3 g Triclosan was mixed in 70 g Glucopon until it became homogeneous, then 75 g 20% Chlorhexidine gluconate was added and the solution was homogenized by the help of a homogenizer and upon adding 854.7 g distilled water, the solution was stirred for 1-1.5 hours. pH value of the solution was made ready by being brought to 5-7 by the help of citric acid or acetic acid. As sated above, the antiviral tests tested antiviral activity against the Human adenovirus type 5 Adenoid 75 strain, Poliovirus Type 1 Chat strain and Human Herpes simplex virus type 1 (HSV-1) MacIntyre strain viruses.

Antiviral Activity Tests of Fabric Surfaces on which the Mixture of Chlorhexidine Gluconate, Glucopon and Triclosan was Applied:

2 cm×2 cm surfaces were cut out from different points of the textile surfaces on which the solution was applied and were placed on 0.5 cm diameter vials. 1 ml virus stock was passed over the surfaces with specified areas. Then the virus stock collected in the vials was sterilized by being passed through a filter with mesh size 0.22 µM. The above-mentioned virus experiment procedure was tested against 3 virus strains for this solution.

Experimental Results

According to the antimicrobial activity test conducted by modified disk diffusion method, it is determined that boron compounds have an effect of preventing growth of all of the tested microorganisms (bacteria, yeasts and fungi). (Table 1)

Hygienic products (sanitary pads, tampons, baby diapers, patient/adult diapers) of 1×1 cm containing or not containing zinc borate, sodium borate, sodium perborate tetrahydrate, borax pentahydrate and disodium octaborate tetrahydrate were prepared in in vitro conditions. Antimicrobial activities of the prepared products were tested by using bacteria (*Escherichia coli, Staphylococcus aureus, Pseudomonas aeruginosa*), yeast (*Candida albicans, Candida glabrata*) and fungi (*Fusarium oxysporum, Botrytis cinerea, Aspergillus niger, Penicillium vinaceum, Penicillium expansum*) isolates. According to the obtained results, it was determined that hygienic products containing zinc borate, sodium borate, sodium perborate tetrahydrate, borax pentahydrate and disodium octaborate tetrahydrate have antimicrobial activity on all of the tested microorganisms while it was observed that the hygienic products with no additives did not show any antimicrobial activity (Table 2).

As a result of the experimental studies, while no growth was observed in sodium borate added sanitary pad and tampon, fungal growth and sporulation were detected in hygienic products with no additives (FIG. 1a, 1b. FIG. 3a, 3b).

While no fungal growth was observed in zinc borate added sanitary pad and tampon, fungal growth and sporulation were detected in hygienic products with no additives (FIG. 2a, 2b).

Since the 10% and 1% suspensions of the tested chlorhexidine gluconate showed cytopathic effect on the cells in the cell culture, the lowest ratio of the said chlorhexidine gluconate which does not show cytopatlic effect, i.e. 0.1%, is used in this study. As a result of the calculations made at the end of the test, it was determined that chlorhexidine gluconate caused at least 4 log reduction in virus titration against Human adenovirus type 5, poliovirus type 1 and herpex simplex (Table 3, Table 4 and Table 5) at all experiment conditions as a result of application at room temperature (20° C.), in clean and polluted media and within 1 and 60 minute application periods.

As a conclusion: these experiment results show that chlorhexidine gluconate is 99.9% active against Human adenovirus type 5 virus, 99.9% active against Poliovirus Type 1 virus and 99.9% active against Herpex simplex virus when used directly without being diluted at room temperature (20° C.) within 1 and 60 minute application periods.

Since the tested 8% Glucopon solution showed cytopathic effect on the cells in the cell culture, the lowest ratio of the said Glucopon which does not show cytopathic effect, i.e. 0.1%, is used in this study. As a result of the calculations made at the end of the test, it was determined that Glucopon did not cause any reduction in virus titration against Herpex simplex virus (Table 6) at the experiment conditions as a result of application at room temperature (20° C.), in clean and polluted media and within 1 and 60 minute application periods.

It was determined as a result of the antiviral activity tests that the mixture of Chlorhexidine gluconate, Glucopon and Triclosan caused at least 4 log reduction in virus titration at all experiment conditions (Table 7, Table 8 and Table 9) as a result of application in clean and polluted media and within 1 and 60 minute application periods.

It was determined as a result of the antiviral activity tests that the fabric surfaces on which the mixture of Chlorhexidine ghconate, Glucopon and Triclosan was applied caused at least 4 log reduction in virus titration at all experiment conditions (Table 10, Table 11 and Table 12) as a result of application in clean and polluted media and within 0 and 60 minute application periods.

In accordance with the TS EN 14476 (MARCH 2007) standards of Turkish Standards Institute (TSE), it is accepted that, when used with any one of the methods of washing, wiping, impregnation (wetting/immersing), this product, whose virucidal activity against Human adenovirus type 5 which is a DNA model virus sample is researched, shows the same virucidal activity against other enveloped or non-enveloped DNA viruses which cannot be practically tested in laboratory such as HBV provided that it is used at least at the above mentioned solubility and periods: and that this product, whose virucidal activity against Poliovirus Type 1 which is an RNA model virus sample is researched, shows the same virucidal activity against other enveloped or non-enveloped RNA viruses (e.g. Ebola, Mers, Sars, etc.) which cannot be practically tested in laboratory such as HCV and HIV provided that it is used at least at the above mentioned solubility and periods.

Irritation tests were performed according to OECD/OCDE 404 method for the prepared antimicrobial products in order to find out whether they cause any irritation on skin. According to the test results, it was observed that no irritation occurred within a period of 14 days.

TABLE 1

Antimicrobial activity of Zinc borate (ZB), Sodium Borate (SB), Sodium perborate tetrahydrate (SPT), Borax pentahydrate (BP) and Disodium octaborate tetrahydrate (DOB) on the tested microorganisms

|  | ZB | SB | SPT | BP | DOB | Positive Control | Negative Control |
|---|---|---|---|---|---|---|---|
| BACTERIA |  |  |  |  |  | Ofloxacin (10 µg/disc) | Distilled Water (20 µl/disc) |
| *Escherichia coli* | +[a] | + | + | + | + | + | −[b] |
| *Staphylococcus aureus* | + | + | + | + | + | + | − |
| *Pseudomonas aeruginosa* | + | + | + | + | + | + | − |
| YEASTS |  |  |  |  |  | Nystatin (30 µg/disc) | Distilled Water (20 µl/disc) |
| *Candida albicans* | + | + | + | + | + | + | − |
| *Candida glabrata* | + | + | + | + | + | + | − |
| FUNGI |  |  |  |  |  | Nystatin (30 µg/disc) | Distilled Water (20 µl/disc) |
| *Aspergillus niger* | + | + | + | + | + | + | − |
| *Fusarium oxysporum* | + | + | + | + | + | + | − |
| *Botrytis cinerea* | + | + | + | + | + | + | − |
| *Penicillium vinaceum* | + | + | + | + | + | + | − |
| *Penicillium expansum* | + | + | + | + | + | + | − |

[a]+sign indicates that the boron compounds had antimicrobial activity.
[b]−sign indicates that there is no antimicrobial activity.

TABLE 2

Antimicrobial activity test results of hygienic products containing of Sodium Borate, Zinc borate, Sodium perborate tetrahydrate, Borax pentahydrate and Disodium octaborate tetrahydrate

|  | Pad | | Tampon | | Baby Diaper | | Adult/Patient Diaper | |
|---|---|---|---|---|---|---|---|---|
|  | With Add. | Without Add. | With Add. | Without Add. | With Add. | Without Add. | With Add. | Without Add. |
| BACTERIA |  |  |  |  |  |  |  |  |
| *Escherichia coli* | +[a] | −[b] | + | − | + | − | + | − |
| *Staphylococcus aureus* | + | − | + | − | + | − | + | − |
| *Pseudomonas aeruginosa* | + | − | + | − | + | − | + | − |
| YEASTS |  |  |  |  |  |  |  |  |
| *Candida albicans* | + | − | + | − | + | − | + | − |
| *Candida glabrata* | + | − | + | − | + | − | + | − |

TABLE 2-continued

Antimicrobial activity test results of hygienic products containing of Sodium Borate, Zinc borate, Sodium perborate tetrahydrate, Borax pentahydrate and Disodium octaborate tetrahydrate

|  | Pad | | Tampon | | Baby Diaper | | Adult/Patient Diaper | |
| --- | --- | --- | --- | --- | --- | --- | --- | --- |
|  | With Add. | Without Add. | With Add. | Without Add. | With Add. | Without Add. | With Add. | Without Add. |
| FUNGI | | | | | | | | |
| *Aspergillus niger* | + | − | + | − | + | − | + | − |
| *Fusarium oxysporum* | + | − | + | − | + | − | + | − |
| *Botrytis cinerea* | + | − | + | − | + | − | + | − |
| *Penicillium vinaceum* | + | − | + | − | + | − | + | − |
| *Penicillium expansum* | + | − | + | − | + | − | + | − |

[a] +sign indicates that the hygienic products containing boron compound had antimicrobial activity.
[b] −sign indicates that the hygienic products not containing boron compound did not have antimicrobial activity.

TABLE 3

Antiviral activity of Chlorhexidine gluconate in HEp-2 cell culture against Human adenovirus type 5 virus Adenoid 75 strain

|  | Reference virus | Chlorhexidine gluconate | | | |
| --- | --- | --- | --- | --- | --- |
|  |  | 1 minute | | 60 minutes | |
|  |  | Clean medium | Polluted medium | Clean medium | Polluted medium |
| Virus titration* | 5.5 | | | | |
| Virus titration with Chlorhexidine gluconate** | | 1.5 | 1.5 | 1.0 | 1.5 |
| Reduction ratio in virus titration*** | | 4.0 | 4.0 | 4.5 | 4.0 |

*Logarithmic $TCID_{50}$ value of the virus in ml.
**Logarithmic $TCID_{50}$ value of the virus treated with Chlorhexidine gluconate at different periods and media.
***Logarithmic TCID50 ratio between the virus titration and the virus titration with Chlorhexidine gluconate

TABLE 4

Antiviral activity of Chlorhexidine gluconate in HEp-2 cell culture against Poliovirus Type 1 virus Chat strain

|  | Reference virus | Chlorhexidine gluconate | | | |
| --- | --- | --- | --- | --- | --- |
|  |  | 1 minute | | 60 minutes | |
|  |  | Clean medium | Polluted medium | Clean medium | Polluted medium |
| Virus titration* | 5.5 | | | | |
| Virus titration with Chlorhexidine gluconate** | | 1.5 | 1.5 | 1.0 | 1.3 |
| Reduction ratio in virus titration*** | | 4.0 | 4.0 | 4.5 | 4.2 |

*Logarithmic $TCID_{50}$ value of the virus in ml.
**Logarithmic $TCID_{50}$ value of the virus treated with Chlorhexidine gluconate at different periods and media.
***Logarithmic TCID50 ratio between the virus titration and the virus titration with Chlorhexidine gluconate

TABLE 5

Antiviral activity of Chlorhexidine gluconate in Vero cell culture against Human Herpes simplex virus type 1 (HSV-1) MacIntyre strain

|  | Reference virus | Chlorhexidine gluconate | | | |
| --- | --- | --- | --- | --- | --- |
|  |  | 1 minute | | 60 minutes | |
|  |  | Clean medium | Polluted medium | Clean medium | Polluted medium |
| Virus titration* | 7.3 | | | | |
| Virus titration with Chlorhexidine gluconate** | | 2.3 | 2.3 | 2.3 | 2.3 |
| Reduction ratio in virus titration*** | | 4 | 4 | 4 | 4 |

*Logarithmic $TCID_{50}$ value of the virus in ml.
**Logarithmic $TCID_{50}$ value of the virus treated with Chlorhexidine gluconate at different periods and media.
***Logarithmic TCID50 ratio between the virus titration and the virus titration with Chlorhexidine gluconate

TABLE 6

Antiviral activity of Glucopon in Vero cell culture against Human Herpes simplex virus type 1 (HSV-1) MacIntyre strain

|  | Reference virus | Chlorhexidine gluconate | | | |
| --- | --- | --- | --- | --- | --- |
|  |  | 1 minute | | 60 minutes | |
|  |  | Clean medium | Polluted medium | Clean medium | Polluted medium |
| Virus titration* | 6.0 | | | | |
| Virus titration with Glucopon** | | 6 | 6 | 6 | 6 |
| Reduction ratio in virus titration*** | | 0 | 0 | 0 | 0 |

*Logarithmic $TCID_{50}$ value of the virus in ml.
**Logarithmic $TCID_{50}$ value of the virus treated with Glucopon at different periods and media.
***Logarithmic TCID50 ratio between the virus titration and the virus titration with Glucopon

TABLE 7

Antiviral activity of the mixture of Chlorhexidine gluconate, Glucopon and Triclosan in HEp-2 cell culture against Poliovirus Type 1 virus Chat strain

|  | Reference virus | Chlorhexidine gluconate, Glucopon and Triclosan mixture | | | |
| --- | --- | --- | --- | --- | --- |
|  |  | 1 minute | | 60 minutes | |
|  |  | Clean medium | Polluted medium | Clean medium | Polluted medium |
| Virus titration* | 5.3 | | | | |
| Virus titration with fabric surface on which the mixture of Chlorhexidine gluconate, Glucopon and Triclosan is applied** | | 1.3 | 1.3 | 1.0 | 1.0 |

TABLE 7-continued

Antiviral activity of the mixture of Chlorhexidine gluconate, Glucopon and Triclosan in HEp-2 cell culture against Poliovirus Type 1 virus Chat strain

|  | Reference virus | Chlorhexidine gluconate, Glucopon and Triclosan mixture | |
|---|---|---|---|
|  |  | 1 minute | 60 minutes |
| Reduction ratio in virus titration*** | 4.0 | 4.0 | 4.3 | 4.3 |

*Logarithmic $TCID_{50}$ value of the virus in ml.
**Logarithmic $TCID_{50}$ value of the virus treated with fabric surfaces on which the mixture of Chlorhexidine gluconate, Glucopon and Triclosan is applied at different periods and media.
***Logarithmic $TCID_{50}$ ratio between the virus titration and the virus titration with fabric surface on which the mixture of Chlorhexidine gluconate, Glucopon and Triclosan is applied

TABLE 8

Antiviral activity of the mixture of Chlorhexidine gluconate, Glucopon and Triclosan in HEp-2 cell culture against Human adenovirus type 5 virus Adenoid 75 strain

|  | Reference virus | Chlorhexidine gluconate, Glucopon and Triclosan mixture | | | |
|---|---|---|---|---|---|
|  |  | 1 minute | | 60 minutes | |
|  |  | Clean medium | Polluted medium | Clean medium | Polluted medium |
| Virus titration* | 5.0 | | | | |
| Virus titration with fabric surface on which the mixture of Chlorhexidine gluconate, Glucopon and Triclosan is applied** | | 1.0 | 1.0 | 1.0 | 1.0 |
| Reduction ratio in virus titration*** | | 4.0 | 4.0 | 4.0 | 4.0 |

*Logarithmic $TCID_{50}$ value of the virus in ml.
**Logarithmic $TCID_{50}$ value of the virus treated with fabric surfaces on which the mixture of Chlorhexidine gluconate, Glucopon and Triclosan is applied at different periods and media.
***Logarithmic $TCID_{50}$ ratio between the virus titration and the virus titration with fabric surface on which the mixture of Chlorhexidine gluconate, Glucopon and Triclosan is applied

TABLE 9

Antiviral activity of the mixture of Chlorhexidine gluconate, Glucopon and Triclosan in Vero cell culture against Human Herpes simplex virus type 1 (HSV-1) MacIntyre strain

|  | Reference virus | Chlorhexidine gluconate, Glucopon and Triclosan mixture | | | |
|---|---|---|---|---|---|
|  |  | 1 minute | | 60 minutes | |
|  |  | Clean medium | Polluted medium | Clean medium | Polluted medium |
| Virus titration* | 6.2 | | | | |
| Virus titration with fabric surface on which Glucopon is applied** | | 2.1 | 2.2 | 2.0 | 2.0 |
| Reduction ratio in virus titration*** | | 4.1 | 4.0 | 4.2 | 4.2 |

*Logarithmic $TCID_{50}$ value of the virus in ml.
**Logarithmic $TCID_{50}$ value of the virus treated with fabric surfaces on which Glucopon is applied at different periods and media.
***Logarithmic $TCID_{50}$ ratio between the virus titration and the virus titration with fabric surface on which Glucopon is applied

TABLE 10

Antiviral activity of the fabric surfaces on which the mixture of Chlorhexidine gluconate, Glucopon and Triclosan is applied in HEp-2 cell culture against Poliovirus Type I virus Chat strain

|  | Reference virus | Fabric surfaces on which the mixture of Chlorhexidine gluconate, Glucopon and Triclosan is applied | | | |
|---|---|---|---|---|---|
|  |  | 0 minute | | 60 minutes | |
|  |  | Clean medium | Polluted medium | Clean medium | Polluted medium |
| Virus titration* | 5.2 | | | | |
| Virus titration with fabric surface on which the mixture of Chlorhexidine gluconate, Glucopon and Triclosan is applied** | | 1.2 | 1.2 | 1.0 | 1.0 |
| Reduction ratio in virus titration*** | | 4.0 | 4.0 | 4.2 | 4.2 |

*Logarithmic $TCID_{50}$ value of the virus in ml.
**Logarithmic $TCID_{50}$ value of the virus treated with fabric surfaces on which the mixture of Chlorhexidine gluconate, Glucopon and Triclosan is applied at different periods and media.
***Logarithmic $TCID_{50}$ ratio between the virus titration and the virus titration with fabric surface on which the mixture of Chlorhexidine gluconate, Glucopon and Triclosan is applied

TABLE 11

Antiviral activity of the fabric surfaces on which the mixture of Chlorhexidine gluconate, Glucopon and Triclosan is applied in HEp-2 cell culture against Human adenovirus type 5 virus Adenoid 75 strain

|  | Reference virus | Fabric surfaces on which the mixture of Chlorhexidine gluconate, Glucopon and Triclosan is applied | | | |
|---|---|---|---|---|---|
|  |  | 0 minute | | 60 minutes | |
|  |  | Clean medium | Polluted medium | Clean medium | Polluted medium |
| Virus titration* | 5.5 | | | | |
| Virus titration with fabric surface on which the mixture of Chlorhexidine gluconate, Glucopon and Triclosan is applied** | | 1.5 | 1.5 | 1.0 | 1.5 |
| Reduction ratio in virus titration*** | | 4.0 | 4.0 | 4.5 | 4.0 |

*Logarithmic $TCID_{50}$ value of the virus in ml.
**Logarithmic $TCID_{50}$ value of the virus treated with fabric surfaces on which the mixture of Chlorhexidine gluconate, Glucopon and Triclosan is applied at different periods and media.
***Logarithmic $TCID_{50}$ ratio between the virus titration and the virus titration with fabric surface on which the mixture of Chlorhexidine gluconate, Glucopon and Triclosan is applied

TABLE 12

Antiviral activity of the fabric surfaces on which the mixture of Chlorhexidine gluconate, Glucopon and Triclosan is applied in Vero cell culture against Human Herpes simplex virus type 1 (HSV-1) MacIntyre strain

|  | Reference virus | Fabric surfaces on which the mixture of Chlorhexidine gluconate, Glucopon and Triclosan is applied | | | |
|---|---|---|---|---|---|
|  |  | 0 minute | | 60 minutes | |
|  |  | Clean medium | Polluted medium | Clean medium | Polluted medium |
| Virus titration* | 6.5 | | | | |

TABLE 12-continued

Antiviral activity of the fabric surfaces on which the mixture of Chlorhexidine gluconate, Glucopon and Triclosan is applied in Vero cell culture against Human Herpes simplex virus type 1 (HSV-1) MacIntyre strain

|  | Fabric surfaces on which the mixture of Chlorhexidine gluconate, Glucopon and Triclosan is applied | | | |
|---|---|---|---|---|
| Reference virus | 0 minute | | 60 minutes | |
| Virus titration with fabric surface on which the mixture of Chlorhexidine gluconate, Glucopon and Triclosan is applied** | 1.2 | 1.2 | 1.2 | 1.2 |
| Reduction ratio in virus titration*** | 5.3 | 5.3 | 5.3 | 5.3 |

*Logarithmic $TCID_{50}$ value of the virus in ml.
**Logarithmic $TCID_{50}$ value of the virus treated with fabric surfaces on which the mixture of Chlorhexidine gluconate, Glucopon and Triclosan is applied at different periods and media.
***Logarithmic $TCID_{50}$ ratio between the virus titration and the virus titration with fabric surface on which the mixture of Chlorhexidine gluconate, Glucopon and Triclosan is applied The present invention is not limited to the above mentioned sanitary pads, tampons, baby diapers, patient/adult diapers, but can be applied on all textile products and all fields wherein similar hygienic products are used.

The invention claimed is:

1. A hygienic product comprising a boron mixture, wherein the boron mixture provides an antimicrobial property; wherein the hygienic product further comprises a poly glycoside surfactant, chlorhexidine gluconate and 5-Chloro-2-(2,4-dichlorophenoxy)phenol, wherein the poly glycoside surfactant, chlorhexidine gluconate, and 5-Chloro-2-(2,4-dichlorophenoxy)phenol provide an antiviral property; wherein the boron mixture comprises a mixture of sodium borate $((Na_2O)(B_2O_3)_5 \cdot 10H_2O)$, zinc borate $(2ZnO \cdot 3B_2O_3 \cdot 3.5H_2O)$, sodium perborate tetrahydrate $(NaBO_3 \cdot 4H_2O)$, borax pentahydrate $(Na_2B_4O_7 \cdot 5H_2O)$ and disodium octaborate tetrahydrate $(Na_2B_8O_{13} \cdot 4H_2O)$.

2. The hygienic product according to claim 1, wherein the boron mixture has a concentration of 0.05-50 mg/cm$^2$.

3. The hygienic product according to claim 2, wherein the poly glycoside surfactant is applied to a surface of the hygienic product at a concentration of 3-10% by weight of the hygienic product.

4. The hygienic product according to claim 3, wherein the chlorhexidine gluconate is applied to the surface at a concentration of 0.1-5% by weight of the hygienic product.

5. The hygienic product according to claim 4, wherein the 5-Chloro-2-(2,4-dichlorophenoxy)phenol is applied to the surface at a concentration of 0.01-0.1% by weight of the hygienic product.

6. The hygienic product according to claim 5, wherein the hygienic product has an antibacterial activity on *Escherichia coli*, *Staphylococcus aureus* and *Pseudomonas aeruginosa* bacteria.

7. The hygienic product according to claim 6, wherein the hygienic product has an anticandidal activity on *Candida albicans* and *Candida glabrata* yeasts.

8. The hygienic product according to claim 7, wherein the hygienic product has an activity on *Fusarium oxysporum, Botrytis cinerea, Aspergillus niger, Penicillium vinaceum* and *Penicillium expansum* fungi.

9. The hygienic product according to claim 8, wherein the hygienic product has an antiviral activity against enveloped and non-enveloped DNA and RNA viruses.

10. The hygienic product according to claim 9, wherein the hygienic product includes a woven textile material, the woven textile material has antimicrobial, antiviral and hydrophilic properties.

11. The hygienic product according to claim 9, the hygienic product is an article selected from the group consisting of a sanitary pad, a tampon, a baby diaper, a patient diaper and an adult diaper.

12. The hygienic product according to claim 9, wherein the hygienic product includes a nonwoven textile material, wherein the nonwoven textile material has antimicrobial, antiviral and hydrophilic properties.

* * * * *